United States Patent
Miller et al.

(10) Patent No.: US 6,645,771 B1
(45) Date of Patent: Nov. 11, 2003

(54) METHOD FOR DETERMINING NO GAS

(75) Inventors: Lewis Sidney Miller, Rugby (GB); David John Walton, Coventry (GB); Andrew Martin McRoberts, Rugby (GB); Andrew Laurence Newton, Birmingham (GB); David Anthony Parry, Warley (GB); Christopher G.D. Sykesud, Sutton Coldfield (GB)

(73) Assignee: Coventry University, Coventry (GB)

( * ) Notice: Subject to any disclaimer, the term of this patent is extended or adjusted under 35 U.S.C. 154(b) by 0 days.

(21) Appl. No.: 09/458,795

(22) Filed: Dec. 10, 1999

Related U.S. Application Data

(63) Continuation of application No. 08/750,886, filed as application No. PCT/GB95/01406 on Jun. 16, 1995, now abandoned.

(30) Foreign Application Priority Data

Jun. 18, 1994 (GB) .............................................. 9412280

(51) Int. Cl.$^7$ .............................................. G01N 21/77
(52) U.S. Cl. ...................... 436/116; 436/164
(58) Field of Search .................... 422/91; 436/116–118, 436/164

(56) References Cited

U.S. PATENT DOCUMENTS 4,941,997 A * 7/1990 Decher et al. .............. 252/586
5,244,812 A * 9/1993 Honeybourne et al. ..... 436/164
5,246,748 A * 9/1993 Gillberg-Laforce et al. ... 428/1

FOREIGN PATENT DOCUMENTS

DE 19513499 A1 * 10/1996

OTHER PUBLICATIONS

Miller, L.S. "Optical gas sensing using Langmuir–Blodgett films" Sensors: Technology, Systems and Applications, IOP Publshing Inc. 1991, pp. 139–143.*

Miller, L.S. "Langmuir–Blodgett films for nonlinear optical applications" Journal of Materials Science, vol. 5, No. 2, Apr. 1994, pp 75–82.*

* cited by examiner

Primary Examiner—Jeffrey Snay
(74) Attorney, Agent, or Firm—Oppenheimer Wolff & Donnelly LLP

(57) ABSTRACT

An optical sensor for detection of gases such as nitrogen oxides includes a thin film of an active material comprising a highly polarisable organic material deposited by the Langmuir-Blodgett technique or otherwise on a substrate and interrogated optically, to detect changes in at least one optical property such as reflectance or complex refractive index. Preferred materials include a specific polysiloxane and low-molecular-mass compounds (FIGS 1 to 5b), having specific electron donating and/or accepting groups, including azobenzenes. The optical change may include a visible colour change.

2 Claims, 3 Drawing Sheets

Polysiloxane I

METHOD FOR DETERMINING NO GAS

Figure 1:
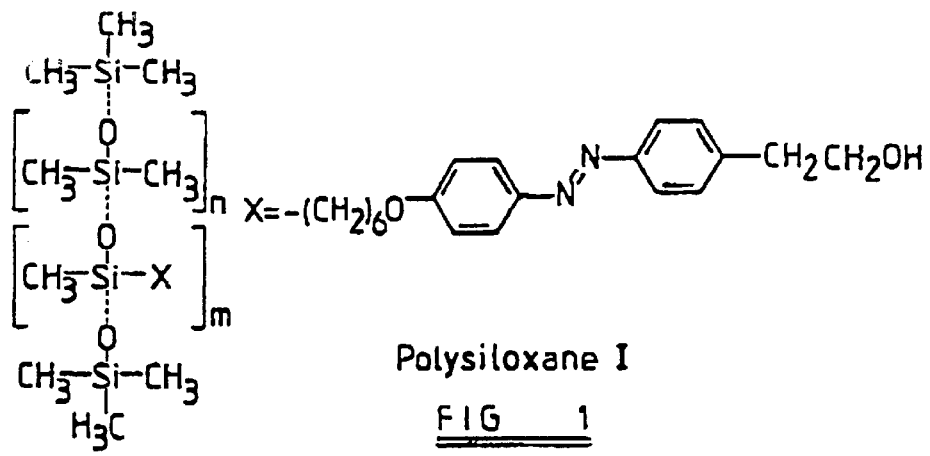

This is a continuation application of application Ser. No. 08/750,886, filed Aug. 4, 1997, now a bandoned which is a continuation of PCT/GB95/B1406 filed Jun. 16, 1995.

This invention relates to an optical gas sensor.

It has been proposed to sense the presence or absence of a gas or gases by Means of the observation of the change in certain optical properties of thin films. Such gas sensors will herein be termed "optical gas sensors".

Hitherto, there have been problems in such optical gas sensors (a) because the magnitude of the observable change has been very low, in other words the sensitivity of the device is low or (b) because the rate of change in the relevant optical property such as reflectance or transmittance is slow, giving the detector a slow response, or (c) because the device structures or signal extraction or processing techniques required to monitor the optical changes are complex or expensive to implement. Materials used in optical gas sensors make a, major contribution to the above factors and have resulted in one or a combination of the problems indicated. Further, after detection of a gas occurs, there has been difficulty in returning the sensor to its original condition, that is the sensor has a slow recovery time.

Some prior art gas sensors of a non-optical type, such as those using tin oxides have had to operate at elevated temperatures which is wasteful of power and could potentially cause flammable gases to ignite. Tin oxide sensors also utilise electrical responses which require electrical connections to the sensor element and thus again constitute a potential hazard. For these reasons, an optically interrogated gas sensor is preferred in many environments.

In a paper, (L. S. Miller, A. L. Newton, C. G. D. Sykesud and D. J. Walton 1991: Optical gas sensing using L B films, Sensors: technology, systems and applications, pp139–143, Adam Hilger (ed K T V Grattan), there is described the use of thin organic films deposited on substrates or on other thin film systems by the Lansgmuir-Blodgett technique, which produces films with a degree of molecular order not normally obtained by other methods and which also leads to reproducible film thicknesses. One such system used an organic film on a silicon substrate. Another utilised a silicon dioxide layer between the silicon and the organic film. The device operated by monitoring the reflectance, preferably of polarised light, from the surface of the layer structure, which is influenced by the optical properties of all the layers and the substrate. The most significant material property of the silicon was its high real refractive index and the most significant material property of the silicon dioxide layer was its lack of absorption and its real refractive index comparable to that of the organic layer, these factors influencing the reflectance obtained because that depends on multiple-beam interference phenomena within the layered structure. In addition, these substrate materials were chosen because they are substantially unreactive to many gases to be sensed.

It has elsewhere been proposed to use reflectance in MOS (Metal Oxide Semiconductor) systems. Interference phenomena may also be utilized to maximise the optical reflectance.

The gas sensing responses are limited by the properties of the thin film materials. Using the techniques outlined in the above-mentioned paper, we have found that phthalocyanines have provided sensitive detection but a very slow response time measured in many minutes. Pyrrole derivatives have provided a quicker response but relatively poor sensitivity.

It is an object of the present invention to provide an optical gas sensor material which has an advantageous combination of high sensitivity and reduced response and recovery times compared with previously proposed materials. It is a further object to provide an optical gas sensor using such a material.

According to the invention there is provided an optical gas sensor comprising an active material deposited on a substrate as a thin film, the active material comprising a highly-polarisable organic material, the sensor being adapted to indicate a change in at least one optical property of the active material due to the presence of a gas.

The active material may be deposited on the substrate by the Langmuir-Blodgett technique.

The highly-polarisable organic material may incorporate a specific electron donating group.

The highly-polarisable organic material may incorporate a specific electron accepting group.

The highly-polarisable organic material may comprise units attached to a polymer backbone.

The polymer backbone may be a polysiloxane.

The active material may be polysiloxane I as defined.

The active material may be an azobenzene derivative.

The active material may be a stilbene derivative.

The sensor may be for detection of a gas comprising one or more oxides of nitrogen, which may be nitrogen dioxide.

The change in optical properties may be a directly visually observable change of colour.

Optical interrogation means may be provided to detect and measure said change in said optical property.

The optical interrogation means may comprise a reflectometer adapted to monitor said change which comprises optical interference effects.

The interrogating optical beam may comprise visible light.

The optical interrogation means may illuminate the film through the substrate.

A conditioning light source may be incorporated for conditioning the active material.

The material may be held at a constant temperature, which may be different from ambient temperature.

The invention also provides a substrate having deposited thereon a thin film of an active material comprising a highly-polarisable organic material for use in an optical gas sensor.

The highly polarisable organic material may comprise an azobenzene derivative which may be a polysiloxane such as Polysiloxane I as herein defined.

The thin film may be deposited by the Langmuir-Blodgett technique.

EXAMPLE

Figure 2:
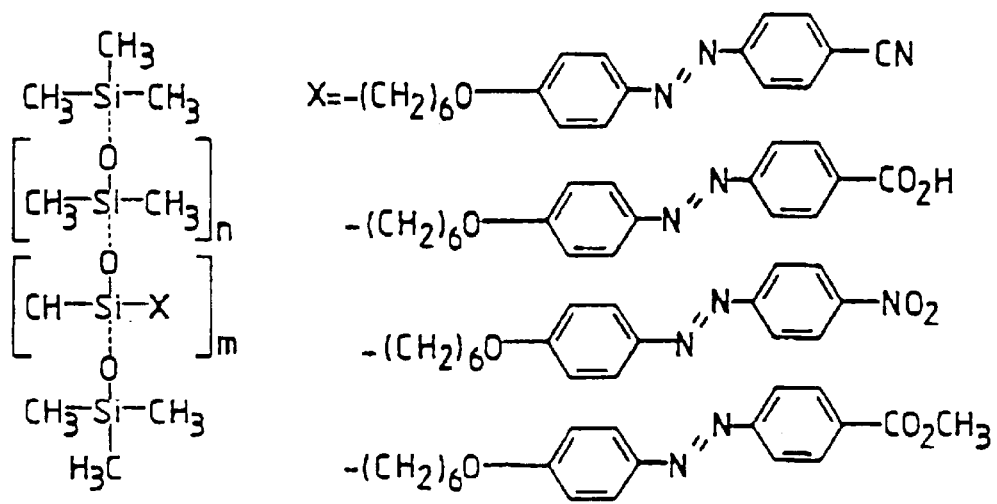
Figure 3:
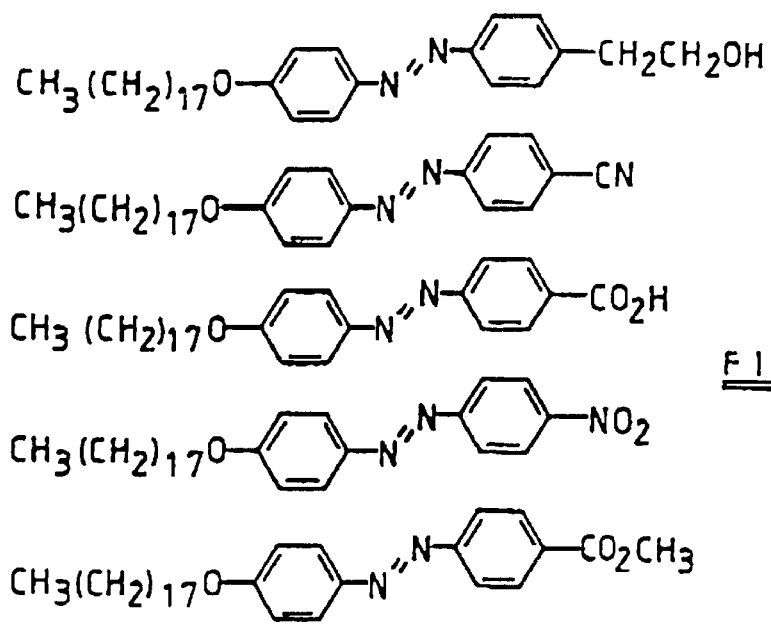
Figure 4:
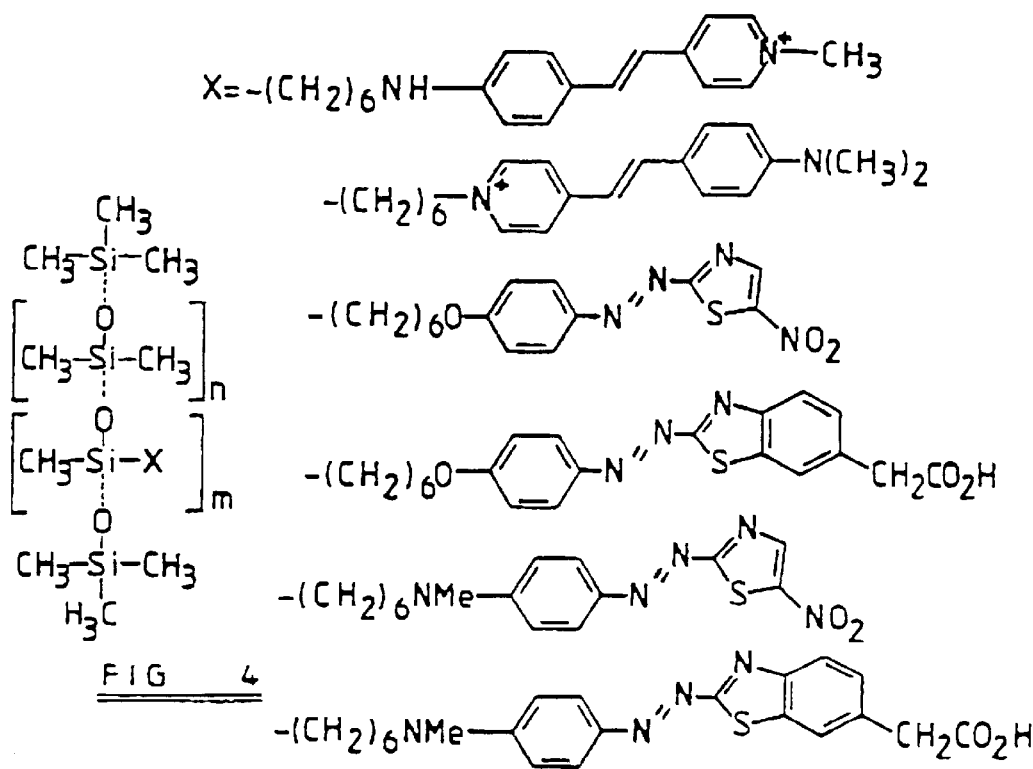
Figure 5A:
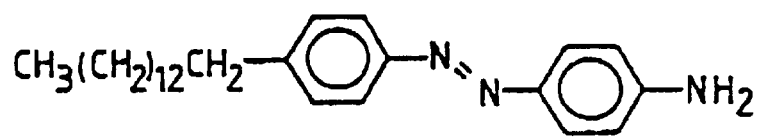
Figure 5B:
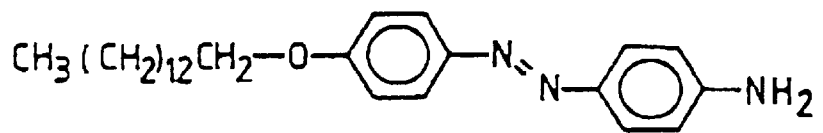

Various examples of the invention will now be described with reference to the accompanying formula drawings in which, FIG. 1 shows a preferred highly polarisable polysiloxane azobenzene derivative designated Polysiloxane I, FIG. 2 shows alternative polysiloxane azobenzenes, FIG. 3 shows alternative highly polarisable azobenzenes in low molecular mass forms, FIG. 4 shows alternative highly polarisable polysiloxanes, FIG. 5a and FIG. 5b show further low molecular mass highly polarisable organic materials for use in the invention, the material of FIG 5a being designated Example 2 and the material of FIG. 5b being designated Example 3 in the following description.

MATERIALS

A preferred material is a polymer or copolymer comprising a polysiloxane backbone to which the active species are attached as side chains. The attachment of active species may be at any or all of the possible attachment points, and attachment may take place via spacer groups to enhance the flexibility of the attachment or to produce other benefits.

The polymer backbone may be hydrophobic.

The active species side-chains may have end-groups at positions remote from the backbone, and these end-groups may have a degree of hydrophilicity or may be hydrophobic.

Alternative polymer backbones may be carbon-based or may be based on other elements, for example polyphosphazenes.

The materials of the invention may be deposited by the Langmuir-Blodgett or related techniques to provide films with a degree of molecular order, or by techniques such as spin-coating or vacuum coating which yield less ordered films. In the case of the LB deposition, the attachment of the active species to the polymer backbone is believed to make the incorporation of the active species into a Langmuir-Blodgett film easier than for related low molecular mass material.

In Example 1, an azobenzene active species in the form indicated in FIG. 1 and termed Polysiloxane I was deposited in a Langmuir-Blodgett film. In that material n=m=6, but other values are allowed. A strong and rapid response to $NO_2$ in air was achieved.

FIG. 2 indicates come proposed alternative forms of the active species of the copolymer, which have acceptors with varying strengths. Up to now, only one type of active species has been employed at one time. It might, however, be possible to use a mixture of active units on each polymer backbone, or a mixture of polymer types, or different layers or regions of polymer types. Use of composite materials or layers may produce a sensor with sensitivity to more than one gas. Data processing may be needed to analyze the detected radiation to determine the gas or gases present on the basis of the differing effects on different materials.

The synthesis of Polysiloxane I as used in this example has been described elsewhere but not for application as a gas sensing material.

The starting polymer is a random copolymer with n=m=6. Synthetic routes are based on the coupling of a suitably substituted diazotised aniline with phenol followed by attachment of an alkene-terminated alkyl chain, typically of six carbons length. These alkenic terminations are then attached to poly(hydrogel)-(dimethyl)-siloxane (PHMS) via a homogeneous platinum-catalysed addition reaction to produce the completed copolymer. Low molecular mass counterparts are prepared by attaching an octadecyl or other chain to give units of the form indicated in FIG. 3.

Some of many alternative active species which might be used in polymeric or low-molecular mass forms are shown in FIG. 4.

In Example 2 a specific low-molecular-mass substance was utilised and gave good response to $NO_2$ in air when deposited as a Langmuir Blodgett film. This substance (FIG. 5a) has a specific electron-donating group ($NH_2$) at the end distant from the hydrocarbon chain.

Example 3, also utilised in a low-molecular-mass form as shown in FIG. 5b, has donating groups at both ends of the active unit and also gives a good response to $NO_2$ in air.

The choice of hydrocarbon chain used in Examples 2 and 3, namely $CH_2(CH_2)_{12}CH_2$, is one possibility for use with other active groups (for example those of FIG. 3 and FIG. 4). Also, alternative chain lengths as indicated, e.g. in FIG. 3, may be used for Examples 2 and 3. The choice of chain length influences deposition properties and is varied to achieve optimum deposition but is not expected to have a major influence on gaseous interactions.

As well as the approach used in the specific Examples 1 to 3, the active species may be attached to other organic units to facilitate deposition as low molecular mass systems or as polymeric systems by the Langmuir-Blodgett or other deposition techniques.

The highly-polarizable active species may comprise a conjugated system allowing electron delocalisation, with or without an electron donating group or groups and with or without an electron accepting group or groups.

Accepting and/or donating groups may require or utilise associated counter-ions incorporated nearby in the material but not covalently bonded to the active species.

METHOD

In order to use the materials exemplified above in gas sensing, the materials are deposited as thin films by the Langmuir-Blodgett or other technique.

The optical properties of the film are determined by its thickness d, and by its complex refractive index:

$$n^* = n - i\,k$$

where n is the real part of the refractive index and k the imaginary part (i being the square root of $-1$). In these materials, the optical properties of the molecules vary with direction so that the resulting n and k of the film will depend on the average molecular orientation, and may vary with direction.

The observed effect may be a direct consequence of a change in k, such as the change in amplitude or wavelength of an absorption maximum not necessarily present before exposure to the gas, or may be the consequent change occurring in n at wavelengths near or longer than that of the appropriate absorption.

Selectivity to different gases may be enhanced by measurements relating to a particular absorption process or processes.

The response could also be modified by any changes in thickness due to the presence of the gas.

Additionally, the effect of the gas on the optical properties of the film may vary as a result of parameters including:

the method of depositing the film;

the thickness of the film;

the wavelength, angle of incidence and polarisation of the incident light;

the temperature;

the prior history including exposure to heat, light, sound and gaseous ambients;

the type and properties of the gas.

The physical technique used for determining the change of optical properties may be thin-film reflectometry, multi-layer reflectometry, optical absorptometry, surface plasmon resonance, waveguide coupling, surface-waveguide or evanescent-wave coupling, phase changes or absorption during waveguide propagation or any other technique capable of detecting a change in the overall optical properties of the deposited film. In some cases direct visual observation of colour changes may be utilised.

The physical technique for determining the optical properties by thin-film reflectometry or multi-layer reflectometry may be as described in the paper referred to above. Possible variants of this include simultaneous interrogation at more than one wavelength, polarisation or incident angle and/or of regions of the device having films of different active species or substrate structure, and the illumination at a fairly broad range of wavelengths and/or angles of incidence. The optical interrogation system may operate in visible or non-visible parts of the electromagnetic spectrum and may use monochromatic light and/or polarized light.

Additionally, all of the above variants could be incorporated in a device which utilised appropriate substrates to facilitate illumination from the back of the substrate. This reduces potential problems due to interference from surface contamination of the film or optical absorption or scattering within the gas above the film, and enables the interrogation system to be completely physically isolated from the gas (which might be inflammable, poisonous or radioactive). One of the major advantages of an optically interrogated system is the ability to isolate the apparatus electrically, for example by the use of optical fibres, but a back illuminated system also has this added advantage of physical separability or isolation.

Alternative substrate materials may include certain wide band-gap semiconductors with a high real refractive index n but low absorption or imaginary index k at the wavelength or wavelengths of interest.

Additionally, all the above variants could be incorporated in a system that utilises optical fibres or similar for optical input and/or output. In this case the tolerance of the device to simultaneous illumination at a range of incident angles would be an especially useful feature, along with the ability to provide remote operation in an inaccessible region or to isolate the gas electrically.

Additionally, the optical device could be incorporated onto an integrated device allowing for optical illumination and detection and perhaps also data processing on a single chip or other integrated electronic system.

Preliminary tests at room temperature, with Examples 1 to 3 have given response times of around 20 seconds, and recovery times of the same order, compared with response times of around 100 minutes and even slower recovery times for the phthalocyanines such as a copper-substituted tetracumyl phenoxy phthalocyanine which has been tested in a similar system as outlined in the paper referred to above.

Furthermore, the present active species defined are capable of a high sensitivity, coupled with fast response and recovery as noted above. Importantly, they have shown little interference from the presence of water vapour.

Additionally, good response and recovery times are maintained for comparatively thick films (greater than 100 nm) whereas films as thin as 6 nm and of consequently lower sensitivity, were required for the phthalocyanine to enhance response times.

Examples 1 to 3 show a significant degree of selectivity, being responsive in particular to $NO_2$. Enhancement of the sensitivity to, low concentrations of the gas to be sensed appears to occur following pre-exposure to sufficient concentrations of that gas, in the present example $NO_2$ in air. Exposure to particular wavelengths and polarisations of light before or during the sensing operation may also influence sensitivity. Such characteristics may enable real-time modification or maintenance of the gas sensor sensitivity.

In a specific example, a 42-layer film of Polysiloxane I on silicon was illuminated with a-polarised light at a wavelength of 520 nm at an angle of incidence of 45° and gave a reflectance change of greater than 50% for 100 ppm of $NO_2$ in air. Similar effects were observed using p-polarised light. Unpolarised light also gives rise to usable reflectance changes. Response and recovery times were short, of the order of 20 seconds.

What is claimed is:

1. A method of detecting the presence of nitrogen oxide gases in a gas sample comprising one or more nitrogen oxide gases and one or more unknown gases including the steps of:

(a) depositing a thin film of an active material comprised of a highly polarizable organic material on a substrate adapted to indicate a change of at least one optical property of the active material due to the presence of the nitrogen oxide gas on the substrate;

(b) contacting the thin film with the gas sample;

(c) directing a light source to the thin film;

(d) monitoring an optical response from the thin film; and (e) correlating the monitored response to the presence of the unknown gas in the gas sample.

2. The method of claim 1 wherein the step of depositing an organic material includes the step of depositing an organic material containing one or more electron-accepting and/or electron-donating groups and a group of the general formula (1):

$$—Ar_1—X_1=X_2—Ar_2— \qquad (1)$$

wherein

Ar$_1$ and Ar$_2$ represent aryl groups; and $X_1$ and $X_2$ represent N or $X_1$ and $X_2$ represent CH.

* * * * *